United States Patent [19]
Ninomiya et al.

[11] Patent Number: 5,536,728
[45] Date of Patent: Jul. 16, 1996

[54] 4-ACYLAMINOPYRIDINE DERIVATIVE

[75] Inventors: Kunihiro Ninomiya, deceased, late of Machida, Japan, by Setsuko Ninomiya, Kouta Ninomiya, Youko Ninomiya heirs; Ken-ichi Saito, Belmont, Mass.; Mamoru Sugano, Hasaki-machi, Japan; Akihiro Tobe, Yokohama, Japan; Yasuhiro Morinaka, Tsuchiura, Japan; Tomoko Bessho, Machida, Japan; Haruko Harada, Yokohama, Japan

[73] Assignee: Mitsubishi Chemical Corporation, Tokyo, Japan

[21] Appl. No.: 355,181

[22] Filed: Dec. 8, 1994

Related U.S. Application Data

[62] Division of Ser. No. 115,257, Sep. 2, 1993, Pat. No. 5,397,785, which is a continuation of Ser. No. 853,519, Mar. 18, 1992, abandoned, which is a continuation of Ser. No. 610,059, Nov. 7, 1990, abandoned.

[30] Foreign Application Priority Data

Nov. 8, 1989 [JP] Japan .................... 1-290915
Nov. 8, 1989 [JP] Japan .................... 1-290916
Nov. 8, 1989 [JP] Japan .................... 1-290918

[51] Int. Cl.⁶ .................. A61K 31/44; C07D 491/048
[52] U.S. Cl. ............... 514/291; 514/279; 514/280; 514/284; 514/285; 514/287; 514/290; 514/297; 546/33; 546/34; 546/35; 546/36; 546/38; 546/39; 546/41; 546/42; 546/47; 546/49; 546/61; 546/62; 546/64; 546/79; 546/80; 546/89; 546/105; 546/106
[58] Field of Search ................. 514/279, 280, 514/284, 285, 287, 290, 297; 546/33, 34, 35, 36, 38, 39, 41, 42, 47, 49, 61, 62, 64, 79, 80, 89, 105, 106

[56] References Cited

U.S. PATENT DOCUMENTS 4,880,819 11/1989 Ninomiya et al. .............. 514/316
4,985,430 1/1991 Morita et al. ................. 514/253

FOREIGN PATENT DOCUMENTS 0273176 7/1988 European Pat. Off. .
0319429 6/1989 European Pat. Off. .
0411534 2/1991 European Pat. Off. .
WO8902740 4/1989 WIPO .

OTHER PUBLICATIONS

G. M. Steinberg et al., "A Hydrophobic Binding Site In Acetylcholinesterase", *Journal of Medicinal Chemistry*, Nov. 1975, pp. 1056–1061.

Primary Examiner—Shailendra Kumar
Attorney, Agent, or Firm—Oblon, Spivak, McClelland, Maier & Neustadt

[57] ABSTRACT

A novel 4-acylaminopyridine derivative represented by the following formula (I) is disclosed.

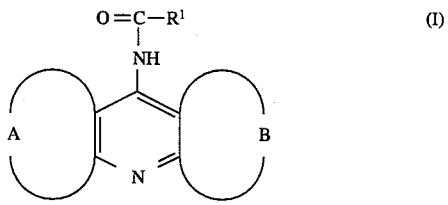

The 4-acylaminopyridine derivative of the present invention is useful as a medicine for treating disturbances of memory such as senile dementia and Alzheimer's disease, since it has an action of directly activating malfunctioned cholinergic neuron.

2 Claims, No Drawings

4-ACYLAMINOPYRIDINE DERIVATIVE

This is a division of application Ser. No. 08/115,257 filed on Sep. 2, 1993, now U.S. Pat. No. 5,397,785, which is a continuation of Ser. No. 07/853,519 filed on Mar. 18, 1992, now abandoned, which is a continuation of Ser. No. 07/610,059 filed on Nov. 7, 1990 now abandoned.

BACKGROUND OF THE INVENTION

The present invention relates to a novel 4-acylaminopyridine derivative and a pharmaceutically acceptable acid-added salt thereof useful for activating a malfunctioned cholinergic neuron.

As a therapeutic treatment for various disturbances of memory such as Alzheimer's disease characterized by malfunction of a cholinergic neuron, has been made an attempt to increase the acetylcholine content in the brain by using an antiacetylcholinesterase. For example, investigation on the use of physostigmine is reported in Neurology, 8, 397(1978). Japanese Patent Application Laid-Open (KOKAI) Nos. 61-148154(1986), 63-141980(1988), 63-225358(1988), 63-238063(1988), 63-239271(1988), 63-284175(1988), 63-297367(1988), 64-73(1989) and 1-132566(1989), EP-A-268871 and International Publication of PCT 88/02256 report that a particular derivative of 9-anminotetrahydroacridine has an antiacetylcholinesterase activity and is therefore useful for treatment of Alzheimer's disease.

Summers reports in The New England Journal of Medicine, 315, 1241(1986) that 9-amino-1,2,3,4-tetrahydroacridine (tacrine) is effective for treatment of Alzheimer's disease when used together with lecithin. However, improvement is still insufficient and it produces undesirable side effects, and therefore, a new therapeutic treatment has been demanded.

As examples of the known 9-acylaminotetrahydroacridines, 9-acylaminotetrahydroacridine is described in Journal of Chemical Society, 634(1947) and 9-chloroacetylaminotetrahydroacridine and 9-dietylaminoacetylaminotetrahydroacridine are described in Chem. listy, 51, 1907(1957). 9-Diemethylaminoacetylaminotetrahydroacridine is described to have a local anesthetic action. In Journal of Medicinal Chemistry, 18, 1056(1975), structure-activity correlation on antiacetylcholinesterase activity of 9-aminotetrahydroacridine derivatives and it is reported that the activity of 9-acetylaminotetrahydroacridine and 9-benzoylaminotetrahydroacridine is 1/1000 of the activity of 9-aminotetrahydroacridine. Some of Japanese Patent Application Laid-Open (KOKAI) Nos. 63-166881(1988), 63-203664(1988), 63-238063(1988), 63-239271(1988), 63-284175(1988), 64-73(1989) and 1-132566(1989) claims a 9-acylaminotetrahydroacridine derivative, however, none of them disclose expressly the synthesis of nor a pharmaceutical activity of a compound having a 9-acylamino group.

The present inventors have made various and extensive studies so as to provide a medicine effective for treatment of senile dementia including Alzheimer's disease. As the result thereof, it has been found that a particular 4-acylaminopyridine derivative and a pharmaceutically acceptable acid-added salt thereof can improve disturbances of memory such as Alzheimer's disease by a mechanism different from that of a conventionally known compound having an antiacetylcholinesterase activity. The present invention has been accomplished based on this finding.

SUMMARY OF THE INVENTION

The present invention provides a 4-acylaminopyridine derivative represented by the following formula (I):

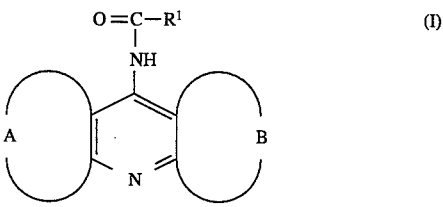

wherein $R^1$ represents a $C_2$–$C_6$ alkyl group or a group represented by the following formula (II):

wherein each of $R^2$ and $R^3$ independently represents a hydrogen atom, $C_1$–$C_6$ alkyl group, $C_3$–$C_6$ cycloalkyl group or

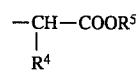

wherein each of $R^4$ and $R^5$ independently represents a hydrogen atom or $C_1$–$C_6$ alkyl group, or $R^2$ and $R^3$ together with the nitrogen atom to which both $R^2$ and $R^3$ are attached represent

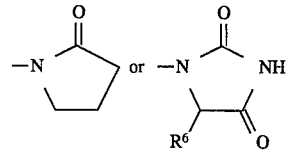

wherein $R^6$ represents a hydrogen atom or $C_1$–$C_6$ alkyl group, and n represents 0 or an integer from 1 to 3;

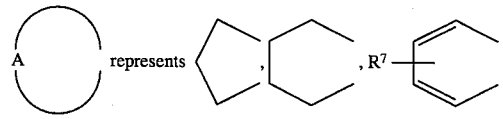

wherein $R^7$ represents a hydrogen atom, $C_1$–$C_6$ alkyl group or halogen atom,

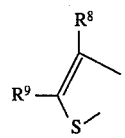

wherein each of $R^8$ and $R^9$ independently represents a hydrogen atom or $C_1$–$C_4$ alkyl group,

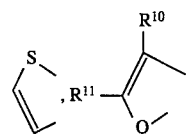

wherein each of $R^{10}$ and $R^{11}$ independently represents a hydrogen atom or a $C_1$–$C_4$ alkyl group,

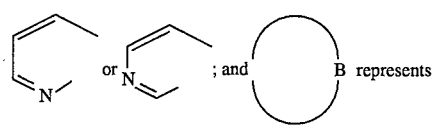 ; and B represents

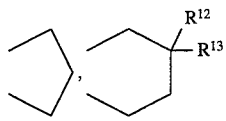 , wherein each of $R^{12}$ and $R^{13}$ independently represents a hydrogen atom or $C_1$–$C_4$ alkyl group or $R^{12}$ and $R^{13}$ may be combined together to form a $C_2$–$C_6$ alkylene group,

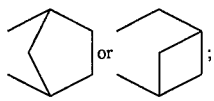 ;

with the proviso that when $R^1$ is a $C_2$–$C_6$ alkyl group or a group represented by the formula (II) wherein one of $R^2$ and $R^3$ is a hydrogen atom or $C_1$–$C_6$ alkyl group and the other of $R^2$ and $R^3$ is a hydrogen atom or -$CH_2COOR^5$ wherein $R^5$ is the same as defined above, or $R^2$ and $R^3$ together with the nitrogen atom to which both $R^2$ and $R^3$ are attached represent

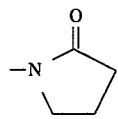

and n is 1 or 2,

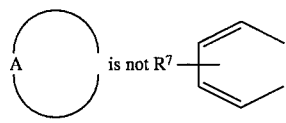

wherein $R^7$ is the same as defined above, or is not

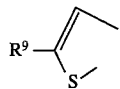

wherein $R^9$ is the same as defined above, and

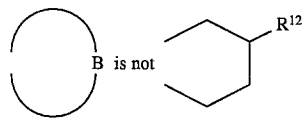

wherein $R^{12}$ represents a hydrogen atom or $C_1$–$C_4$ alkyl group or is not

 ;

and a pharmaceutically acceptable acid-added salt thereof.

The present invention further provides a pharmaceutical composition comprising a pharmaceutically effective amount of a 4-acylaminopyridine derivative represented by the formula (I) or a pharmaceutically acceptable acid-added salt thereof, and a pharmaceutically acceptable adjuvant.

The present invention still further provides a process for producing a 4-acylaminopyridine derivative represented by the formula (I) and a pharmaceutically acceptable acid-added salt thereof.

DETAILED DESCRIPTION OF THE INVENTION

The 4-acylaminopyridine derivative according to the present invention is represented by the formula (I) shown above.

In the formula (I), as examples of $C_2$–$C_6$ alkyl group (alkyl group having 2 to 6 carbon atoms) represented by $R^1$, ethyl group, n-propyl group, isopropyl group, n-butyl group, sec-butyl group, tert-butyl group, n-pentyl group and n-hexyl group may be mentioned. Among these, a $C_2$–$C_4$ alkyl group is particularly preferable.

Examples of $C_1$–$C_6$ alkyl group represented by each of $R^2$ to $R^7$ are methyl group, ethyl group, n-propyl group, isopropyl group, n-butyl group, sec-butyl group, tert-butyl group, n-pentyl group and n-hexyl group. Among these, a $C_1$–$C_4$ alkyl group is preferable.

As $C_3$–$C_6$ cycloalkyl group represented by each of $R^2$ and $R^3$, cyclopropyl group, cyclobutyl group, cyclopentyl group and cyclohexyl group may be mentioned.

A halogen atom represented by $R^7$ is exemplified by fluorine atom, chlorine atom, bromine atom and iodine atom.

As examples of $C_1$–$C_4$ alkyl group represented by each of $R^8$ to $R^{13}$, methyl group, ethyl group, n-propyl group, isopropyl group, n-butyl group, sec-butyl group and tert-butyl group may be mentioned.

In the present invention, among the compounds represented by the formula (I), is preferred a compound wherein $R^1$ represents a $C_2$–$C_6$ alkyl group or a group represented by the following formula (II):

 (II)

wherein $R^2$ represents a hydrogen atom or $C_1$–$C_8$ alkyl group, $R^3$ represents a hydrogen atom, $C_1$–$C_6$ alkyl group, $C_3$–$C_6$ cycloalkyl group or

wherein each of $R^4$ and $R^5$ independently represents a hydrogen atom or $C_1$–$C_6$ alkyl group, or $R^2$ and $R^3$ together with the nitrogen atom to which both $R^2$ and $R^3$ are attached represent

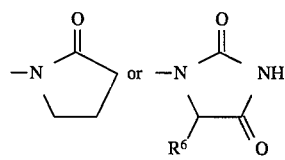

wherein $R^6$ represents a hydrogen atom or $C_1$–$C_6$ alkyl group, and n represents 0 or an integer from 1 to 3;

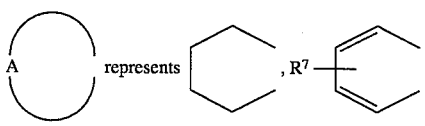

wherein R⁷ represents a hydrogen atom, $C_1$–$C_6$ alkyl group or halogen atom,

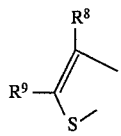

wherein each of $R^8$ and $R^9$ independently represents a hydrogen atom or $C_1$–$C_4$ alkyl group, or

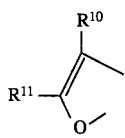

wherein each of $R^{10}$ and $R^{11}$ independently represents a hydrogen atom or a $C_1$–$C_4$ alkyl group; and

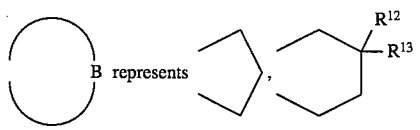

wherein each of $R^{12}$ and $R^{13}$ independently represents a hydrogen atom or $C_1$–$C_4$ alkyl group or $R^{12}$ and $R^{13}$ may be combined together to fore a $C_2$–$C_6$ alkylene group, or

More preferred is a compound wherein

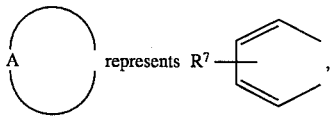

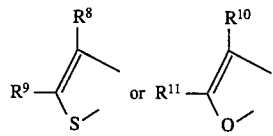

wherein $R^7$ to $R^{11}$ are the same as defined above.

The acid-added salt of the compound represented by the formula (I) is preferred to be pharmaceutically and physiologically acceptable. For example, inorganic acid-added salts such as hydrochloride, hydrobromide, hydroiodide, sulfate and phosphate, and organic acid-added salts such as oxalate, maleate, fumarate, lactate, malate, citrate, tartrate, benzoate, methanesulfonate and camphorsulfonate may be mentioned. The compound represented by the formula (I) and the acid-added salt thereof can be present in the form of hydrate or solvate. These hydrate and solvate are also included in the compound of the present invention.

A process for producing the compound of the present invention will now be explained.

The compound represented by the formula (I) is produced by, for example, any of the following processes (1) to (5).

Process (1)

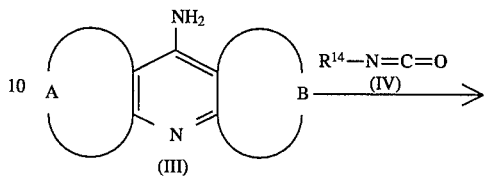

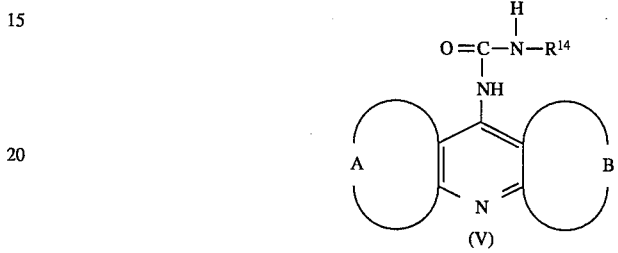

In the above reaction scheme,

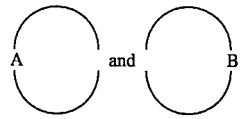

in the formulae (III) and (V) are the same as defined above, and $R^{14}$ in the formulae (IV) and (V) represents a $C_1$–$C_6$ alkyl group or $C_3$–$C_6$ cycloalkyl group. Through the process (1), the compound of the present invention represented by the formula (V) can be produced by reacting a primary aromatic amine of the formula (III) with an isocyanate compound of the formula (IV).

As the reaction solvent, a halogen solvent such as dichloromethane, 1,2-dichloroethane and 1,1,2,2-tetrachloroethane or an inert polar solvent such as tetrahydrofuran, dioxane, acetonitrile, dimethylformamide, dimethyl sulfoxide and N-methylpyrrolidone may be preferably used.

The reaction may be carried out at a temperature from 0° to 120° C., preferably 20° to 80° C.

Process (2)

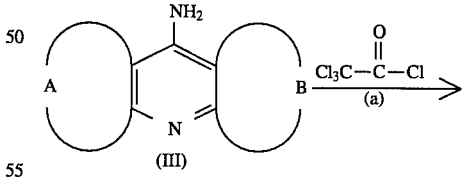

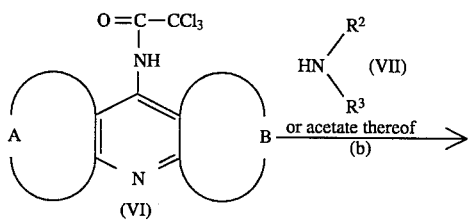

-continued

Process (2)

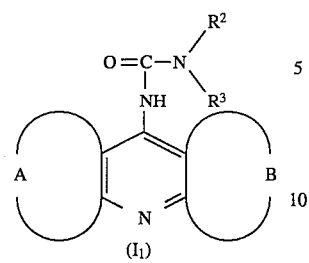

In the above reaction scheme,

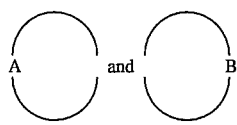

in the formulae (III), (VI) and (I₁) and $R^2$ and $R^3$ in the formulae (VII) and (I₁) are the same as defined above. Through the process (2), the compound of the present invention represented by the formula (I₂) can be produced by reacting a compound of the formula (III) with excess trichloroacetyl chloride (reaction (a)) to obtain and isolate a trichloroacetamide compound of the formula (VI), and then reacting the compound of the formula (VI) with an amine of the formula (VII) or acetate thereof (reaction (b)).

The reaction (a) is carried out by using trichloroacetyl chloride also as the solvent at a temperature from 80° to 115° C., preferably from 100° to 115° C.

The reaction (b) is carried out preferably in an inert solvent such as tetrahydrofuran, dioxane, acetonitrile, dimethylformamide, dimethyl sulfoxide, N-methylpyrrolidone, etc. The reaction temperature is from 0° to 100° C., preferably from 0° to 50° C. when the amine is used, and from 50° to 160° C., preferably from 100° to 150° C. when the acetate of the amine is used.

Process (3)

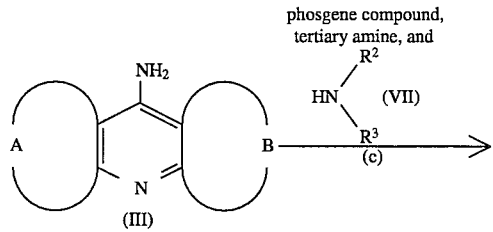

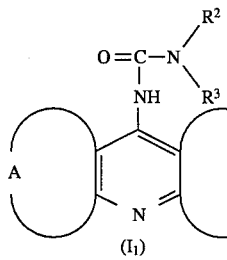

In the above reaction scheme,

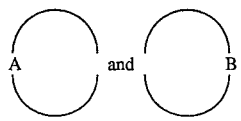

in the formulae (III) and (I₁), and $R^2$ and $R^3$ in the formulae (VII) and (I₁) are the same as defined above. Through the process (3), the compound of the present invention represented by the formula (I₁) can be produces. More in detail, the compound of the formula (III) is dissolved in an inert solvent such as methylene chloride, 1,2-dichloroethane, 1,1,2,2-tetrachloroethane, benzene, toluene, xylene, tetrahydrofuran and dioxane, then, a phosgene compound such as ditrichloromethyl carbonate, phosgene and trichloromethyl chloroformate is added to the solution, followed by the addition of a tertiary amine such as triethylamine. The thus obtained solution is added dropwise to a solvent containing the amine represented by the formula (VII) to give the compound represented by the formula (I₁). As the solvent for dissolving the amine represented by the formula (VII), tetrahydrofuran, dioxane, acetonitrile and alcohols are preferable, and it is possible to use a mixed solvent of water with at least one of the above-described solvents, if necessary.

In the above reaction (c), the addition of the phosgene compound and the addition of the tertiary amine are carried out at a temperature from −10° to 50° C., preferably from 0° to 30° C. The reaction with the amine represented by the formula (VII) is carried out at a temperature from −20° to 30° C., preferably from −10° to 20° C.

Process (4)

(1) By reacting the compound represented by the formula (III):

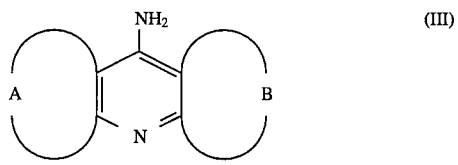 (III)

wherein

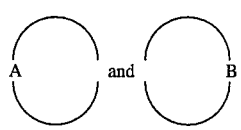

have the same meanings as defined in the above formula (I), with a reactive derivative of the compound represented by the formula (VIII):

 (VIII)

wherein $R^{15}$ represents a $C_2$–$C_6$ alkyl group, the compound represented by the formula (I₂) of the present invention can be obtained.

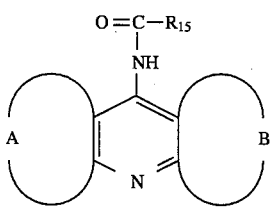

(I₂)

wherein

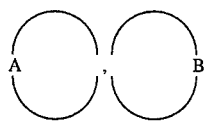

and $R^{15}$ have the same meanings as defined above.

Examples of the reactive derivatives of the compound of the formula (VIII) are preferably symmetric acid anhydrides or acid halides, particularly acid chloride. The reaction is carried out in the presence of of an inert solvent such as benzene, toluene, xylene, 1,2-dichloroethane, 1,1,2,2-tetrachloroethane, etc., or by using excessive amounts of symmetric acid anhydrides or acid halides as a solvent. When the symmetric acid anhydrides are used, a tertiary amine such as pyridine may be preferably used. The reaction is carried out at a temperature in the range of 30° to 150° C., preferably 50° to 120° C.

(2) After processing the compound represented by the above formula (III) with an equimolar Amount or more of sodium hydride to prepare a sodium salt, reacting it with an ester compound represented by the formula (IX):

$$R^{16}-\underset{\underset{O}{\|}}{C}-O-R^{17} \quad (IX)$$

wherein $R^{16}$ represents

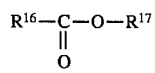

(wherein i represents an integer from 1 to 3), and $R^{17}$ represents a methyl group or an ethyl group, to obtain the compound represented by the formula (I₃):

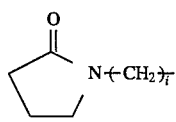

(I₃)

wherein

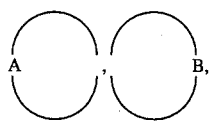

and $R^{16}$ have the same meanings as defined above.

As the solvent, preferred are tetrahydrofuran, dioxane, acetonitrile, dimethylformamide, N-methylpyrrolidone, dimethylsulfoxide, etc. The reaction is carried out at a temperature in the range of 10° to 80° C., preferably 30° to 60° C.

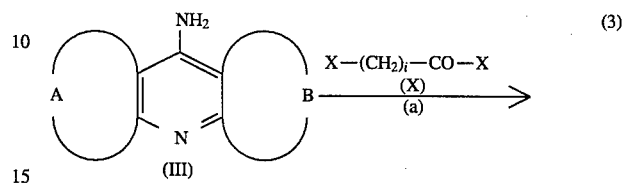

(3)

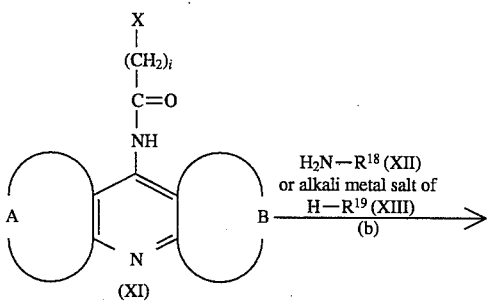

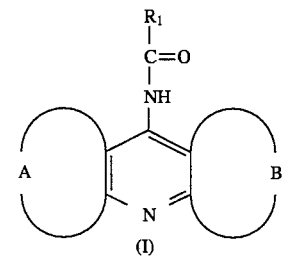

(I)

wherein X represents a chlorine atom or a bromine atom; i represents 1, 2 or 3;

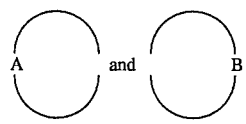

have the same meanings as defined in the formula (I); $R^{18}$ in the formula (XII) represents a $C_1$–$C_6$ alkyl group or

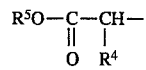

(wherein $R^4$ and $R^5$ have the same meanings as defined in the formula (I); $R^{19}$ in the formula (XIII) represents

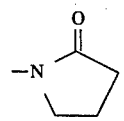

By the above two steps of the reaction formulae, the compound of the formula ($I_4$) or ($I_5$) can be synthesized.

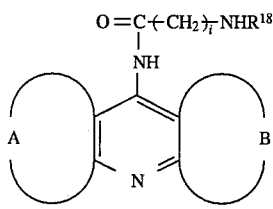

($I_4$)

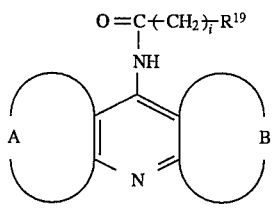

($I_5$)

In the above formulae ($I_4$) and ($I_5$),

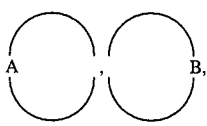

$R^{18}$, $R^{19}$ and i have the same meanings as defined above.

That is, an acyl halide compound of the formula (X) is reacted with the compound of the formula (III) to obtain the compound of the formula (XI) [step (a)]. Then, to the compound of the formula (XI), the compound of the formula (XII) is reacted, or else a compound which is a sodium salt obtained by treating the compound of the formula (XIII) with sodium hydride [step (b)], the corresponding compound (I) can be obtained.

The step (a) is carried out by using an excessive amount of acyl halide also as the solvent, or by using an inert solvent such as benzene, toluene, xylene, 1,2-dichloroethane, 1,1,2,2-tetrachloroethane, etc., at a temperature in the range of 50° to 150° C., preferably 70° to 120° C.

The step (b) is carried out by using an excessive amount of amine also as the solvent, or by using an alcoholic solvent such as methanol, ethanol, n-propanol, isopropanol, n-butenol, etc., or a solvent such as tetrahydrofuran, dioxane, acetonitrile, dimethylformamide, dimethylsulfoxide, etc., at a temperature in the range of 0° to 150° C., preferably 20° to 100° C. When the sodium salt of the compound of the formula (XIII) is reacted, the reaction is carried out by using a solvent such as tetrahydrofuran, dioxane, acetonitrile, dimethylformamide, dimethylsulfoxide, etc., at a temperature in the range of 0° to 120° C., preferably 20° to 80° C.

Process (5)

The compound where $R^1$ is a group represented by the formula (II) and $R^2$ and $R^3$ together with the nitrogen atom to which both $R^2$ and $R^3$ are attached represent

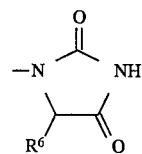

wherein $R^6$ is the same as defined above, i.e. the compound represented by the formula ($I_6$), can be produced according to the following reaction scheme.

(XIV)

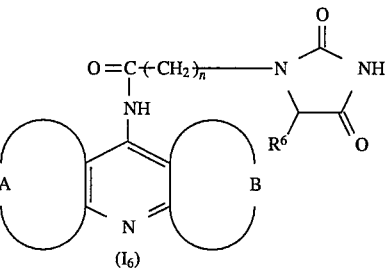

($I_6$)

wherein

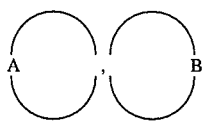

and $R^6$ are the same as defined above and $R^{20}$ represents a $C_1$–$C_4$ alkyl group.

In more detail, the compound of the formula ($I_6$) can be obtained by heating the compound of the formula (XIV) together with 1 to 10 equivalents of urea in the presence or absence of a solvent.

The compound of the formula (XIV), the starting material, can be obtained by the process described in process (4).

As the solvent for producing the compound of the formula ($I_6$), an inert polar solvent such as dimethyl sulfoxide, dimethylformamide, dimethylacetamide and N-methylpyrrolidone is preferred.

The reaction temperature is from 120° to 190° C., preferably from 140° to 170° C.

The starting compound represented by the formula (III) can be easily synthesized by, for example, the methods described in (a) Tetrahedron Letters, 1277(1963), (b) Collect. Czech. Chem. Commun., 42, 2802(1977), and (c) Acta Chemica Scandinavica, B, 33, 313(1979) and similar methods thereto.

It is also possible to synthesize the starting compound (III) in accordance with the methods described in Japanese Patent Application Laid-Open (KOKAI) Nos. 61-148154(1986), 63-141980(1988), 63-166881(1988), 63-203664(1988), 63-225358(1988), 63-238063(1988), 63-239271(1988), 63-297367(1988), 64-73(1989), 1-132566(1989) and EP-A-268871.

The acid-added salt of the compound represented by the formula (I) can be easily obtained by a known method to prepare an acid-added salt of a quinoline or pyridine based compound.

Some of the starting compound represented by the formula (III) for producing the compound of the present invention, which were produced according to the methods described in the above references are shown in Table 1 below.

TABLE 1

| Compound No. | A | B | Melting Point (°C.) |
|---|---|---|---|
| 1 | 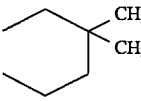 |  | 199–200 |
| 2 | 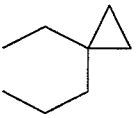 |  | 162–163 |
| 3 |  |  | 203–204 |
| 4 |  |  | 141–143 |
| 5 |  |  | 201–204 |
| 6 | 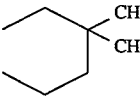 | 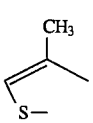 | 206–207 |
| 7 | 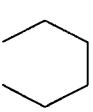 |  | 156–158 |
| 8 |  |  | 213–214 |
| 9 |  |  | 238–242 |
| 10 |  |  | 138–139 |

The compound of the present invention is used as a therapeutic medicine by administrating it singly or in the form of a mixture with a pharmaceutically accept, able carrier. The composition is determined based on the solubility and property of the compound to be used as the active ingredient, the administration route and dosage regimen. For example, the compound of the present invention may be orally administered in the form of granule, subtilized granule, powder, tablet, hard capsule, soft capsule, syrup, emulsion, suspension and solution. The compound of the present invention may be also administered intravenously, intramuscularly or subcutaneously by injection. The compound of the present invention may be prepared to an injectable powder and injected after dissolving or suspending in an appropriate solvent when used.

It is possible to use an organic or inorganic, solid or liquid carrier or diluent, which is suitable for oral, intestinal, parenteral or local administration, together with the compound of the present invention. As a vehicle for a solid preparation, lactose, sucrose, starch, talc, cellulose, dextrin, kaolin and calcium carbonate are usable. A liquid preparation for oral administration, i.e. emulsion, syrup, suspension, solution, etc., contains a usual diluent such as water, vegetable oil, etc. The liquid preparation can contain an auxiliary such as a hnmectant, suspending agent, sweetening agent, aromatic, coloring agent, preservative etc. in addition to the inert diluent. The liquid preparation may be encapsulated in an absorbable wall substance such as gelatin. As a solvent or a suspending agent used for preparing a parenteral preparation such as an injection preparation, water, propylene glycol, polyethylene glycol, benzyl alcohol, ethyl oleate and lecithin may be mentioned. The preparation may be carried out by an ordinary method.

The daily clinical dosage of the compound of the present invention in oral administration is usually 1 to 1000 mg, preferably 1 to 100 mg for an adult. It is preferable to appropriately increase or decrease the dose depending upon the age of patient, condition of disease, condition of patient, and whether or not another medicine is administered. The daily dose of the compound of the present invention may be administered at once, or in two or three portions with appropriate interval. Intermittent administration thereof is also applicable.

The daily dosage of the compound of the present invention in injection is 0.1 to 100 mg, preferably 0.1 to 50 mg for an adult.

Although the antiacetylcholinesterase activity of the compound represented by the formula (I) is $\frac{1}{100}$ of that of known 9-aminotetrahydroacridine, the compound of the present invention can reactivate the presynaptic site of the cholinergic neuron to enhance the neurotransmission. More precisely, the compound of the present invention improves the reduced high-affinity choline-uptake in the hippocampak synaptosome of a rat treated with AF64A (ethylcholine aziridinium ion; J. Pharmacol. Exp. Ther., 222, 140(1982) and Neuropharmacol., 26, 361(1982)) intra-cerebroventricularly (Test Example 1 below). This kind of action is not observed in 9-aminotetrahydroacridine.

Further, the compound of the present invention is very low in toxicity and scarcely produces side effect in comparison with 9-aminotetrahydroacridine, and therefore, the compound of the present invention can be a useful medicine for treating disturbances of memory such as Alzheimer's disease.

The compound of the present invention represented by the formula (I) is a pharmaceutically active and valuable compound. Especially, the compound of the present invention is useful as a medicine for treating disturbances of memory such as senile dementia and Alzheimer's disease, since it has an action on the activating malfunctioned cholinergic neuron.

In senile dementia, in particular, Alzheimer's disease, the function of the cholinergic neuron in the bran is decreased, and it is recognized that there is a good correlation between the deficit in the cholinergic neuron and the degree of disturbances in memory.

As reported by Fisher (J. Pharmacol. Exp. Ther., 222, 140(1982)) and Leventer (Neuropharmacol, 26, 361(1987)), AF64A causes long-term malfunction selectively on cholinergic neuron, and disturbance of memory and learning is observed in a rat to which AF64A is administered. Such a rat is used as a good model of Alzheimer's disease. Therefore, from the above pharmacological results, the compound of the present invention is considered to be useful for treating senile dementia including Alzheimer's disease.

EXAMPLES:

The present invention will be explained in more detail with reference to the following examples, but it is to be understood that the present invention is not restricted to the following examples and any modification is possible within the scope of the present invention.

Example 1:

Synthesis of
N-(3-methyl-5,6,7,8-tetrahydrothieno[2,3
-b]-quinolin4-yl)butanamide To 4.37 g of 4-amino-3-methyl -5,6,7,8-tetrahydrothieno[2,3-b]quinoline, were added 8 ml of pyridine and 12.7 g of n-butyric anhydride and the mixture was refluxed for 13 hours. The reaction mixture was evaporated to dryness under a reduced pressure, and dissolved in 170 ml of methanol and 40 ml of ethanol. To the solution, was added 70 ml of concentrated ammonia water and the reaction was carried out at 65° C. for 1.5 hours.

The solvent was evaporated under a reduced pressure and 100 ml of chloroform, 100 ml of water and 5 ml of concentrated ammonia water were added, followed by stirring. The chloroform layer was dried over anhydrous sodium sulfate.

The chloroform solution was evaporated. The obtained product was purified by silica gel column chromatography (chloroform-methanol) and was recrystallized from chloroform-diethyl ether to obtain 5.11 g of the titled compound having the melting point of 200° to 202° C.

Examples 2 to 13:

Each of the compounds listed in Table 2 was synthesized in the same manner as in Example 1.

TABLE 2

| Example No. | A | B | Melting Point (°C.) |
|---|---|---|---|
| 2 | cyclopentene | cyclopentane | 201–203 |
| 3 | cyclohexene | cyclopentane | 192–194 |
| 4 | cyclohexene | cyclohexane with two CH$_3$ groups | 183–184 |
| 5 | cyclohexene | spiro[2.5] (cyclopropane-cyclohexane) | 175–176 |
| 6 | thiophene (S—) | cyclopentane | 168–170 |
| 7 | thiophene (S—) | cyclohexane with two CH$_3$ groups | 164–165 |
| 8 | CH$_3$—C(CH$_3$)=C—S— | cyclohexane | 205–206 |
| 9 | S-containing ring | cyclohexane | 188–190 |
| 10 | CH$_3$—C(CH$_3$)=C—O— | cyclohexane | 204–206 |
| 11 | pyridine (N) | cyclohexane | 88–91 |
| 12 | CH$_3$—C(CH$_3$)=C—O— | cyclopentane | 193–194 |
| 13 | CH$_3$—C(CH$_3$)=C—O— | bicyclic | 159–161 |

Example 14:

Synthesis of N-(2,3-dimethyl-5,6,7,8-tetrahydrofuro[2,3-b]-quinolin-4-yl)isobutanamide The titled compound having the melting point of 245° to 246° C. was obtained in the same way as in Example 10 except for using isobutyric anhydride in place of n-butyric anhydride.

Example 15:

Synthesis of 2-(2-oxopyrrolidin-1-yl)-N-(3-methyl-5,6,7,8-tetrahydrothieno[2,3-b]quinolin-4-yl)acetamide Into a suspension of 1.26 g of sodium hydride (60% content) in 15 ml of N-methylpyrrolidone, was added 3.28 g of 4-amino-3-methyl -5,6,7,8-tetrahydrothieno[2,3-b] quinoline at room temperature. The mixture was heated to 50° C. and stirred for 40 minutes. Thereafter, 4.72 g of methyl 2-oxo-1-pyrrolidine acetate was added dropwise to the mixture at 50° C. over a period of 30 minutes. After the stirring at 50° C. for 20 minutes, the mixture was cooled to 15° C. and poured into 130 ml aqueous solution containing 13.5 g of ammonium chloride.

After extraction of the solution with 100 ml of chloroform, the extract was dried over anhydrous sodium sulfate, followed by evaporation to dryness. The resultant product was added with ethyl acetate, pulverized and filtered. The crude crystals were recrystallized from chloroform-ethyl acetate to obtain 4.31 g of the titled compound having the melting point of 244° to 246° C.

Examples 16 to 29:

Each of the compounds listed in Table 3 was synthesized in the same way is in Example 15.

TABLE 3

| Example No. | A | B | Melting Point (°C.) |
|---|---|---|---|
| 16 | cyclopentyl | cyclopentyl | 217–220 |
| 17 | cyclohexyl | cyclopentyl | 222–225 |
| 18 | cyclohexyl | cyclohexyl | 244–246 |
| 19 | cyclohexenyl | cyclohexyl with CH₃/CH₃ | 203–204 |
| 20 | cyclohexenyl | spiro-cyclopropyl cyclopentyl | 192–194 |
| 21 | thiophene (S−) | cyclopentyl | 168–170 |
| 22 | thiophene (S−) | cyclohexyl with CH₃/CH₃ | 161–163 hydrochloride |
| 23 | CH₃,CH₃-substituted thiophene (S−) | cyclohexyl | 216–218 |
| 24 | S-containing ring | cyclohexyl | 210–212 |
| 25 | CH₃,CH₃-substituted furan (O−) | cyclohexyl | 213–215 |
| 26 | pyridyl (N) | cyclohexyl | 189–191 |
| 27 | pyridyl (N) | cyclohexyl | 193–195 |
| 28 | CH₃,CH₃-substituted furan (O−) | cyclopentyl | 216–217 |

TABLE 3-continued

[Structure: O=C—CH₂—N(pyrrolidinone); NH attached to central pyridine with rings A and B fused, N in pyridine, with additional rings A and B below]

| Example No. | A | B | Melting Point (°C.) |
|---|---|---|---|
| 29 | CH₃, CH₃—C=C—O— (methyl groups on alkene with O) | norbornyl | 159–161 |

Example 30:

Synthesis of N-(5,6,7,8-tetrahydrothieno[2,3-b]-quinolin-4-yl)urea

A mixture of 8.17 g of 4-amino-5,6,7,8-tetrahydrothieno[2,3-b]quinoline and 90 ml of trichloroacetyl chloride was refluxed for 4 hours. The mixture was cooled to 25° C. and 30 ml of 1,2-dichloroethane was added thereto. The crystals were filtered out and washed with 1,2-dichloroethane.

The suspension of the crystals in 200 ml of chloroform and 120 ml of water was added with 5 ml of concentrated ammonia water. After the chloroform layer was dried over anhydrous sodium sulfate, it was purified by silica gel column chromatography (chloroform). By recrystallization from chloroform-n-heptane, 11.84 g of N-(5,6,7,8-tetrahydrothieno[2,3-b]-quinolin-4-yl)trichloroacetamide having the melting point of 176° to 178° C. was obtained.

In 20 ml of N-methylpyrrolidone, was dissolved 3.5 g of the obtained compound. After adding 6.2 g of ammonium acetate to the solution, the reaction was carried out at 150° C. for 30 minutes. After cooled to 30° C., the reaction mixture was added with 100 ml of water and 50 ml of chloroform, followed by stirring. The pH of the aqueous layer of the mixture was adjusted to 10 with concentrated ammonia water.

The insoluble matters were collected by filtration and washed with chloroform and water, followed by recrystallization from ethanol -1,1,2,2-tetrachloroethane-ethyl acetate to obtain 0.73 g of the titled compound having the melting point of 260° to 262° C.

Example 31:

Synthesis of N-methyl-N'-(5,6,7,8-tetrahydrothieno[2,3-b]quinolin-4-yl)urea

In 120 ml of 1,1,2,2-tetrachloroethane, was dissolved 2.45 g of 4-amino-5,6,7,8-tetrahydrothieno[2,3-b]quinoline, and 1.78 g of ditrichloromethyl carbonate was added to the solution at a temperature from 20° to 30° C.

After adding 6.7 g of triethylamine at a temperature from 20° to 30° C., the mixture was stirred for one hour at room temperature.

Separately, 70 ml of 40% methanol solution of methylamine was cooled at −10° C. The reaction mixture was added dropwise to the methanol solution at 0° C. and heated to 30° C. in one hour.

Then, 150 ml of water and 120 ml of chloroform were added to the mixture and the insoluble matters were filtered out, followed by recrystallization from methanol-chloroform to obtain 2.49 g of the titled compound having the melting point of 253° to 255° C.

Examples 32 to 37;

Compounds shown in Table 4 were synthesized in the same way as in Example 31.

TABLE 4

[Structure: O=C—N(R²)(R³); NH attached to central pyridine with rings A and B fused, N in pyridine; additional rings A and B below]

| Example No. | A | B | R² | R³ | Melting Point (°C.) |
|---|---|---|---|---|---|
| 32 | CH₃-cyclohexenyl | cyclohexyl | H | H | 216–218 |

TABLE 4-continued

[Structure: tetrahydroacridine derivative with O=C-N(R²)(R³) attached via NH, with rings A and B fused to central pyridine ring]

| Example No. | A | B | R² | R³ | Melting Point (°C.) |
|---|---|---|---|---|---|
| 33 | Cl-phenyl | cyclohexyl | H | H | 220~235 Decomposed |
| 34 | Cl-phenyl | cyclohexyl | CH₃ | CH₃ | 211~216 |
| 35 | thienyl (S—) | cyclohexyl | CH₃ | CH₃ | 215~218 |
| 36 | thienyl (S—) | cyclohexyl | H | cyclopropyl | 248~250 |
| 37 | (CH₃)₂C=C(CH₃)-S— | cyclohexyl | H | H | 292~294 |

Example 38:

Synthesis of N-[(1,2,3,4-tetrahydroacridin-9-yl)amino-carbonylmethyl]-L-alanine ethyl ester To 5 g of 9-chloroacetylamino-1,2,3,4-tetrahydroacridine, was added 22 g of L-alanine ethyl ester and the reaction was continued for 30 minutes at 100° C. After cooled to room temperature, the reaction mixture was added with 100 ml of chloroform and 100 ml of water and stirred. The chloroform layer was dried over anhydrous sodium sulfate and purified by silica gel column chromatography (chloroform-methanol), followed by recrystallization from chloroform-n-hexane to obtain 5.9 g of the titled compound having the melting point of 101° to 102° C.

Example 39:

Synthesis of N-[(1,2,3,4-tetrahydroacridin-9-yl) aminocarbonylmethyl]-L-alanine

Into 12 ml of 1N aqueous solution of sodium hydroxide, was added 2 g of the compound obtained in Example 38 at room temperature, and the reaction was continued for 2 hours. To the reaction mixture, was added 15 ml of 1N hydrochloric acid at a temperature not higher than 15° C. to precipitate white crystals. The crystals were collected by filtration, washed with water and dried to obtain 1.42 g of the titled compound having the melting point of 238° to 242° C. (decomposed).

Examples 40 to 42:

Compounds shown in Table 5 were synthesized in the same way as in Example 38 or 39.

TABLE 5

| Example No. | A | B | R² | R³ | Melting Point (°C.) |
|---|---|---|---|---|---|
| 40 | benzene | cyclohexane | H | —CH—CO₂CH₃<br>\|<br>CH<br>/\<br>CH₃  CH₃<br>S-isomer | 139–140 |
| 41 | benzene | cyclopentane | H | —CH—CO₂CH₃<br>\|<br>CH<br>/\<br>CH₃  CH₃<br>S-isomer | 127–130 |
| 42 | benzene | cyclohexane | H | —CH—COOH<br>\|<br>CH<br>/\<br>CH₃  CH₃<br>S-isomer | 223–226 Decomposed |

Reference Example 1:

Synthesis of 2-chloro-N-(3-methyl-5,6,7,8-tetrahydrothieno[-2,3-b]quinolin-4-yl)acetamide To 12.7 g of 4-amino-3-methyl-5,6,7,8-tetrahydrothieno[2,3-b]quinoline, was added 40 ml of chloroacetyl chloride, and the mixture was refluxed for 40 minutes. The oil bath was removed and the reaction mixture was added with 50 ml of 1,2-dichloroethane and cooled to 25° C. The precipitated crystals were collected by filtration and washed with 1,2-dichloroethane. The crystals were suspended in a mixed solvent of 250 ml of chloroform, 55 ml of water and 60 ml of ethanol, and 4.3 ml of concentrated ammonia water was added thereto. The suspension was heated to 40° C. to dissolve substantially all the crystals.

The chloroform layer was dried over anhydrous sodium sulfate and concentrated to a volume of about 100 ml. The chloroform solution was added with 40 ml of n-heptane and cooled, followed by filtration to obtain 8.2 g of the titled compound having the melting point of 233° to 236° C.

Example 43:

Synthesis of 2-cyclopropylamino-N-(3-methyl-5,6,7,8-tetrahydrothieno[2,3-b]quinolin-4-yl)acetamide To 12 ml of t-butanol and 25 ml of dimethylformamide, was added 2.1 g of the compound obtained in Reference Example 1. Then, 9 ml of cyclopropylamine was added and the reaction was carded out at 100° C. for 30 minutes.

The reaction mixture was evaporated to dryness under a reduced pressure, then, 100 ml of chloroform, 30 ml of water and 5 ml of concentrated ammonia water were added, followed by stirring. The chloroform layer was dried over anhydrous sodium sulfate and purified by silica gel column chromatography (chloroform-methanol), followed by recrystallization from ethyl acetate to obtain 1.52 g of titled compound having the melting point of 141° to 144° C.

Examples 44 to 52:

Compounds shown in Table 6 were synthesized in the same way as in Example 43.

TABLE 6

$$\underset{\underset{B}{\underset{N}{\bigcirc}}}{\overset{O=C-CH_2-N-©}{\underset{NH}{\overset{|}{\underset{A}{\bigcirc}}}}}$$

| Example No. | A | B | © | Melting Point (°C.) |
|---|---|---|---|---|
| 44 | CH₃-C(=)-S- (with CH₃) | cyclohexyl | —CH(CH₃)—CO₂C₂H₅  S-isomer | Amorphous solid |
| 45 | cyclohexyl | cyclopentyl | —CH₃ | 142–145 |
| 46 | cyclohexyl | cyclopentyl | —CH(CH₃)—CO₂C₂H₅  S-isomer | 110–111 |
| 47 | thienyl (S—) | cyclopentyl | —CH₃ | 146–149 |
| 48 | CH₃—C(=)(CH₃)—O— | cyclohexyl | —CH₃ | 141–143 |
| 49 | CH₃—C(=)(CH₃)—O— | cyclohexyl | —CH₂—CO₂CH₃ | 147–149 |
| 50 | CH₃—C(=)(CH₃)—O— | cyclohexyl | —CH₂—CO₂H | 221–230 (Decomposed) |
| 51 | CH₃—C(=)(CH₃)—O— | cyclohexyl | —CH(CH₃)—CO₂H  S-isomer | 245–250 |
| 52 | CH₃—C(=)(CH₃)—O— | cyclohexyl | —CH(CH(CH₃)₂)—CO₂H  S-isomer | 218–222 |

Example 53:

Synthesis of 2-((S)-5-methyl-2,4-dioxoimidazolidin-1-yl)-N-(1,2,3,4-tetrahydroacridin-9-yl)acetamide In 9 ml of N-methylpyrrolidone, was dissolved 3.9 g of the compound obtained in Example 38, and 2.64 g of urea was further added thereto. The reaction was carried out at 160° C. for one hour. The reaction mixture was cooled to 80° C. and 100 ml of water was added. The precipitated crystals were collected by filtration and dissolved in a mixture of 5 ml of methanol and 150 ml of chloroform. The solution was dried over anhydrous sodium sulfate and evaporated to dryness. The obtained product was recrystallized from ethanol-ethyl acetate to obtain 2.44 g of the titled compound having the melting point of 260° to 263° C.

Examples 54 to 60:

Compounds shown in Table 7 were synthesized in the same way as in Example 53:

further cooled to 25° C. after addition of 90 ml of water. The precipitated crystals were collected by filtration and recrystallized from methanol-water to obtain 0.84 g of the titled

TABLE 7

| Example No. | A | B | R⁶ | Melting Point (°C.) |
|---|---|---|---|---|
| 54 |  |  | H | 280–287 Decomposed |
| 55 |  | 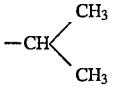 | −CH(CH₃)(CH₃) S-isomer | 219–223 |
| 56 |  |  CH₃ | H | 279–283 Decomposed |
| 57 |  |  | H | 285–295 Decomposed Hydrochloride |
| 58 | 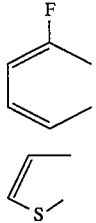 |  | H | 216–263 |
| 59 |  |  | H | 298–301 |
| 60 |  |  CH₃ | H | 270–274 |

Example 61:

Synthesis of 2-((S)-5-methyl-2,4-dioxoimidazolidin-1-yl)-N-(3-methyl-5,6,7,8-tetrahydrothieno[2,3-b]quinolin-4-yl)-acetamide In 8 ml of N-methylpyrrolidone, was dissolved 2.5 g of the compound obtained in Example 44, and 8 g of urea was further added. The reaction was continued at 160° C. for 40 minutes. The reaction mixture was cooled to 80° C. and compound having the melting point of 273° to 277° C.

Examples 62 to 65:

Compound shown in Table 8 were synthesized in the same way as in Example 61.

Compounds shown in Table 9 and Table 10 can be synthesized in the same way as described in Examples above.

TABLE 8

| Example No. | A | B | © | Melting Point (°C.) |
|---|---|---|---|---|
| 62 | cyclohexyl | cyclopentyl | hydantoinyl with CH₃ | 197–198 |
| 63 | (CH₃)₂C=C(O-)— | cyclohexyl | hydantoinyl (CH₂) | 242–245 |
| 64 | (CH₃)₂C=C(O-)— | cyclohexyl | hydantoinyl with CH₃ | 274–281 |
| 65 | (CH₃)₂C=C(O-)— | cyclohexyl | hydantoinyl with CH(CH₃)CH₃ | 158–160 |

TABLE 9

| Compound No. | A | B | R¹ |
|---|---|---|---|
| 66 | cyclopentyl | cyclopentyl | —CH(CH₃)₂ |
| 67 | cyclohexyl | cyclohexyl | —C₃H₇ |

TABLE 9-continued
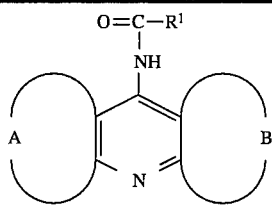
| Compound No. | A | B | R¹ |
|---|---|---|---|
| 68 |  | 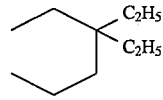 C₂H₅ / C₂H₅ | —C₃H₇ |
| 69 |  | 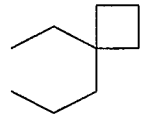 | —C₃H₇ |
| 70 |  | 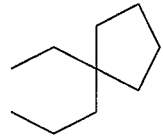 | —C₃H₇ |
| 71 |  | 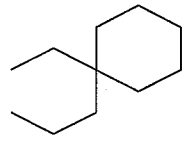 | —C₃H₇ |
| 72 |  | 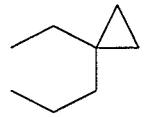 | —C₃H₇ |
| 73 |  |  | —C₂H₅ |
| 74 |  |  | —CH(CH₃)₂ |
| 75 |  |  | —C₄H₉ |
| 76 |  |  | —CH₂—CH(CH₃)—CH₃ |
| 77 |  |  | —CH(CH₃)—C₂H₅ |
| 78 |  |  | —C(CH₃)₃ |

TABLE 9-continued
| Compound No. | A | B | R¹ |
|---|---|---|---|
| 79 |  |  | —C₃H₇ |
| 80 | 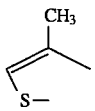 |  | —C₃H₇ |
| 81 | 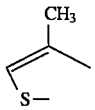 | 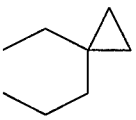 | —C₃H₇ |
| 82 | 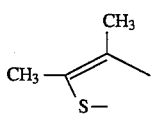 |  | —C₃H₇ |
| 83 | 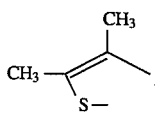 | 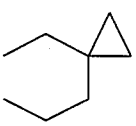 | —C₃H₇ |
| 84 |  |  | —C₃H₇ |
| 85 |  | 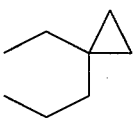 | —C₃H₇ |
| 86 | 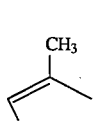 |  | —C₃H₇ |
| 87 | 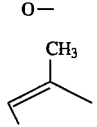 |  | —C₃H₇ |
| 88 | 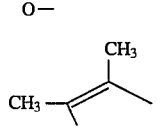 | 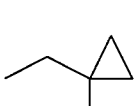 | —C₃H₇ |
| 89 | 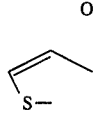 |  | —C₃H₇ |

TABLE 9-continued
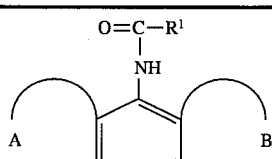
| Compound No. | A | B | R¹ |
|---|---|---|---|
| 90 | 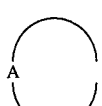 | 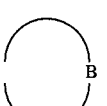 | $-C_3H_7$ |
| 91 | 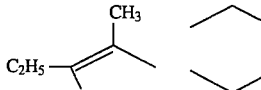 | 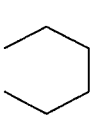 | $-C_3H_7$ |
| 92 | 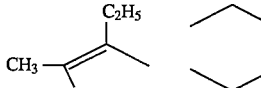 | 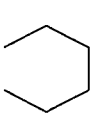 | $-C_3H_7$ |
| 93 | 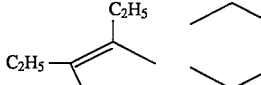 | 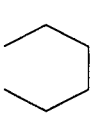 | $-C_3H_7$ |
| 94 |  | 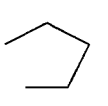 | $-C_3H_7$ |
| 95 |  | 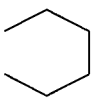 | $-C_3H_7$ |
TABLE 10
| Compound No. | A | B | R² | R³ | n |
|---|---|---|---|---|---|
| 96 | 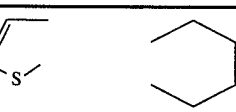 |  | H | $-C_2H_5$ | 0 |

TABLE 10-continued

| Compound No. | A | B | R² | R³ | n |
|---|---|---|---|---|---|
| 97 | thiophene | cyclohexyl | H | —C₃H₇ | 0 |
| 98 | thiophene | cyclohexyl | H | —CH(CH₃)₂ | 0 |
| 99 | thiophene | cyclohexyl | H | —C₄H₉ | 0 |
| 100 | thiophene | cyclohexyl | H | —CH₂—CH(CH₃)₂ | 0 |
| 101 | thiophene | cyclohexyl | H | —CH(CH₃)—C₂H₅ | 0 |
| 102 | thiophene | cyclohexyl | H | cyclobutyl | 0 |
| 103 | 2-methylthiophene | cyclohexyl | H | H | 0 |
| 104 | 2-methylthiophene | cyclohexyl | —CH₃ | —CH₃ | 0 |
| 105 | 2-methylthiophene | cyclohexyl | H | H | 0 |
| 106 | 2-methylthiophene | cyclohexyl | —CH₃ | —CH₃ | 0 |
| 107 | 2,3-dimethyl-4,5-dihydrothiophene | cyclohexyl | —CH₃ | —CH₃ | 0 |

TABLE 10-continued

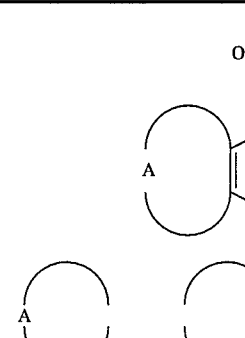

| Compound No. | A | B | R² | R³ | n |
|---|---|---|---|---|---|
| 108 | thiophene | cyclopentane | H | H | 0 |
| 109 | thiophene | cyclopentane | —CH₃ | —CH₃ | 0 |
| 110 | cyclohexene | cyclohexane | H | H | 0 |
| 111 | cyclohexene | cyclohexane | H | —CH₃ | 0 |
| 112 | cyclohexene | cyclohexane | H | —C₂H₅ | 0 |
| 113 | cyclohexene | cyclohexane | H | —C₃H₇ | 0 |
| 114 | cyclohexene | cyclohexane | H | —CH(CH₃)₂ | 0 |
| 115 | cyclohexene | cyclohexane | —CH₃ | —CH₃ | 0 |
| 116 | methyl-cyclohexene | cyclohexane | H | H | 0 |
| 117 | fluoro-cyclohexene | cyclohexane | H | H | 0 |
| 118 | cyclohexene | cyclopentane | CH₃ | H | 0 |

TABLE 10-continued

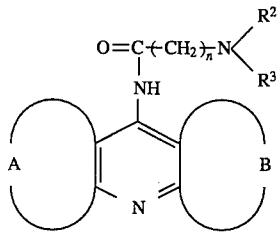

| Compound No. | A | B | R² | R³ | n |
|---|---|---|---|---|---|
| 119 | benzene | cyclopentane | CH₃ | CH₃ | 0 |
| 120 | CH₃-benzene | cyclopentane | H | H | 0 |
| 121 | F-benzene | cyclopentane | H | H | 0 |
| 122 | Cl-benzene | cyclopentane | H | H | 0 |
| 123 | cyclopentane | cyclopentane | H | —CH₃ | 1 |
| 124 | cyclohexane | cyclopentane | H | —CH₃ | 1 |
| 125 | cyclohexane | cyclohexane | H | —CH₃ | 1 |
| 126 | benzene | CH₃,CH₃-cyclohexane | H | —CH₃ | 1 |
| 127 | benzene | spiro[cyclopropane-cyclopentane] | H | —CH₃ | 1 |
| 128 | thiophene | cyclopentane | H | —CH₃ | 1 |
| 129 | thiophene | CH₃,CH₃-cyclohexane | H | —CH₃ | 1 |

TABLE 10-continued
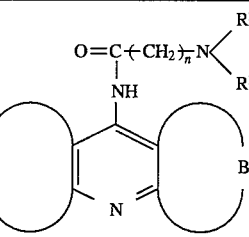

TABLE 10-continued

| Compound No. | A | B | R² | R³ | n |
|---|---|---|---|---|---|
| 140 | CH₃-C(CH₃)=CH-S- (with CH₃ on one carbon) | cyclohexyl | H | cyclobutyl | 1 |
| 141 | (CH₃)₂C=C(CH₃)-S- | cyclopentyl | H | —CH₃ | 1 |
| 142 | (CH₃)₂C=C(CH₃)-S- | cyclohexyl | H | —CH₃ | 1 |
| 143 | (CH₃)₂C=C(CH₃)-S- | cyclopropyl-CH₂CH₂- | H | —CH₃ | 1 |
| 144 | S-CH=CH- | cyclopentyl | H | —CH₃ | 1 |
| 145 | S-CH=CH- | cyclohexyl | H | —CH₃ | 1 |
| 146 | S-CH=CH- | cyclopropyl-CH₂CH₂- | H | —CH₃ | 1 |
| 147 | CH₃-C(=CH-)-O- | cyclopentyl | H | —CH₃ | 1 |
| 148 | CH₃-C(=CH-)-O- | cyclohexyl | H | —CH₃ | 1 |
| 149 | (CH₃)₂C=C(CH₃)-O- | cyclopentyl | H | —CH₃ | 1 |

TABLE 10-continued $$O=C-(CH_2)_n-N\begin{matrix}R^2\\R^3\end{matrix}$$
(attached via NH to pyridine bearing rings A and B)

| Compound No. | A | B | R² | R³ | n |
|---|---|---|---|---|---|
| 150 | (CH₃)(CH₃)C=C(CH₃)–O– | cyclohexyl | H | –CH₃ | 1 |
| 151 | pyridyl (N top) | cyclohexyl | H | –CH₃ | 1 |
| 152 | pyridyl (N bottom) | cyclohexyl | H | –CH₃ | 1 |
| 153 | pyridyl (N bottom) | cyclopropyl-CH₂- | H | –CH₃ | 1 |
| 154 | cyclopentyl | cyclopentyl | H | –CH₂–COOC₂H₅ | 1 |
| 155 | cyclohexyl | cyclopentyl | H | –CH₂COOCH₃ | 1 |
| 156 | cyclohexyl | cyclopentyl | H | –CH₂–COOC₂H₅ | 1 |
| 157 | cyclohexyl | cyclopentyl | H | –CH(CH₃)–COOCH₃ | 1 |
| 158 | cyclohexyl | cyclopentyl | H | –CH(CH(CH₃)₂)–COOCH₃ | 1 |
| 159 | cyclohexyl | cyclopentyl | H | –CH(CH(CH₃)₂)–COOC₂H₅ | 1 |
| 160 | cyclohexadienyl | cyclohexyl | H | –CH(CH₃)–COOCH₃ | 1 |

TABLE 10-continued $$\underset{A}{\bigcirc}\underset{N}{\overset{NH-C(=O)(CH_2)_n-N{<}_{R^3}^{R^2}}{\bigcirc}}\underset{B}{\bigcirc}$$

| Compound No. | A | B | R² | R³ | n |
|---|---|---|---|---|---|
| 161 | phenyl | cyclohexyl | H | —CH(C₂H₅)—COOCH₃ | 1 |
| 162 | 3-F-phenyl | cyclohexyl | H | —CH(CH₃)—COOC₂H₅ | 1 |
| 163 | 2-F-phenyl | cyclohexyl | H | —CH(CH₃)—COOC₂H₅ | 1 |
| 164 | 3-Cl-phenyl | cyclohexyl | H | —CH(CH₃)—COOC₂H₅ | 1 |
| 165 | phenyl | norbornyl | H | —CH(CH(CH₃)₂)—COOCH₃ | 1 |
| 166 | 2-F-phenyl | norbornyl | H | —CH(CH₃)—COOC₂H₅ | 1 |
| 167 | thienyl | cyclohexyl | H | —CH(CH₃)—COOH | 1 |
| 168 | thienyl | cyclohexyl | H | —CH(CH₃)—COOC₂H₅ | 1 |
| 169 | thienyl | cyclohexyl | H | —CH(CH(CH₃)₂)—COOCH₃ | 1 |
| 170 | 2-CH₃-thienyl | cyclohexyl | H | —CH(CH₃)—COOC₂H₅ | 1 |
| 171 | thienyl | norbornyl | H | —CH(CH₃)—COOH | 1 |

TABLE 10-continued $$O=C(CH_2)_n-N\begin{matrix}R^2\\R^3\end{matrix}$$
attached to pyridine core with rings A and B, NH linker

| Compound No. | A | B | R² | R³ | n |
|---|---|---|---|---|---|
| 172 | thiophene | cyclopentane | H | —CH(CH₃)—COOC₂H₅ | 1 |
| 173 | thiophene | cyclohexane | H | —CH(CH₃)—COOH | 1 |
| 174 | thiophene | cyclohexane | H | —CH(CH₃)—COOC₂H₅ | 1 |
| 175 | methyl-thiophene | cyclohexane | H | —CH(CH₃)—COOC₂H₅ | 1 |
| 176 | benzene | gem-dimethylcyclohexane | H | —CH₂—COOC₂H₅ | 1 |
| 177 | benzene | spiro-cyclopropane-cyclohexane | H | —CH₂—COOC₂H₅ | 1 |
| 178 | thiophene | cyclopentane | H | —CH₂—COOC₂H₅ | 1 |
| 179 | thiophene | gem-dimethylcyclohexane | H | —CH₂—COOC₂H₅ | 1 |
| 180 | thiophene | spiro-cyclopropane-cyclohexane | H | —CH₂—COOC₂H₅ | 1 |
| 181 | methyl-thiophene | cyclopentane | H | —CH₂—COOC₂H₅ | 1 |
| 182 | methyl-thiophene | cyclohexane | H | —CH₂—COOC₂H₅ | 1 |

TABLE 10-continued

| Compound No. | A | B | R² | R³ | n |
|---|---|---|---|---|---|
| 183 | CH₃-C(CH₃)=CH-S- | 1,1-dimethylcyclohexyl | H | $-CH_2-COOC_2H_5$ | 1 |
| 184 | CH₃-C(CH₃)=CH-S- | 1-ethylcyclopropyl | H | $-CH_2-COOC_2H_5$ | 1 |
| 185 | (CH₃)₂C=C(CH₃)-S- | cyclopentyl | H | $-CH_2-COOC_2H_5$ | 1 |
| 186 | (CH₃)₂C=C(CH₃)-S- | cyclohexyl | H | $-CH_2-COOC_2H_5$ | 1 |
| 187 | (CH₃)₂C=C(CH₃)-S- | 1-ethylcyclopropyl | H | $-CH_2-COOC_2H_5$ | 1 |
| 188 | -S-CH=CH- | cyclopentyl | H | $-CH_2-COOC_2H_5$ | 1 |
| 189 | -S-CH=CH- | cyclohexyl | H | $-CH_2-COOC_2H_5$ | 1 |
| 190 | -S-CH=CH- | 1-ethylcyclopropyl | H | $-CH_2-COOC_2H_5$ | 1 |
| 191 | CH₃-C(CH₃)=CH-O- | cyclopentyl | H | $-CH_2-COOC_2H_5$ | 1 |
| 192 | CH₃-C(CH₃)=CH-O- | cyclohexyl | H | $-CH_2-COOC_2H_5$ | 1 |

TABLE 10-continued

| Compound No. | A | B | R² | R³ | n |
|---|---|---|---|---|---|
| 193 | (CH₃)(CH₃)C=C(CH₃)–O– | cyclopentyl | H | –CH₂–COOC₂H₅ | 1 |
| 194 | (CH₃)(CH₃)C=C(CH₃)–O– | cyclohexyl | H | –CH₂–COOC₂H₅ | 1 |
| 195 | (CH₃)(CH₃)C=C(CH₃)–O– | spiro[cyclopropane-cyclopentane] | H | –CH₂–COOC₂H₅ | 1 |
| 196 | pyridyl (N top) | cyclohexyl | H | –CH₂–COOC₂H₅ | 1 |
| 197 | pyridyl (N bottom) | cyclohexyl | H | –CH₂–COOC₂H₅ | 1 |
| 198 | cyclopentyl | cyclopentyl |  | –N(hydantoinyl) | 1 |
| 199 | cyclohexyl | cyclopentyl |  | –N(hydantoinyl) | 1 |
| 200 | cyclohexyl | cyclopentyl |  | –N(isopropyl-hydantoinyl) | 1 |
| 201 | cyclohexadienyl | 1,1-dimethylcyclohexyl |  | –N(hydantoinyl) | 1 |

TABLE 10-continued

| Compound No. | A | B | R² | R³ | n |
|---|---|---|---|---|---|
| 202 | benzene | 1-propylcyclopropyl | | -N(C(=O)NHC(=O)CH₂-) (hydantoinyl) | 1 |
| 203 | thiophene | cyclopentyl | | -N(C(=O)NHC(=O)CH₂-) (hydantoinyl) | 1 |
| 204 | thiophene | 1,1-dimethylpentyl | | -N(C(=O)NHC(=O)CH₂-) (hydantoinyl) | 1 |
| 205 | thiophene | 1-propylcyclopropyl | | -N(pyrrolidin-2-on-1-yl) | 1 |
| 206 | thiophene | 1-propylcyclopropyl | | -N(C(=O)NHC(=O)CH₂-) (hydantoinyl) | 1 |
| 207 | 2-methylthiophene | cyclopentyl | | -N(pyrrolidin-2-on-1-yl) | 1 |
| 208 | 2-methylthiophene | cyclopentyl | | -N(C(=O)NHC(=O)CH₂-) (hydantoinyl) | 1 |
| 209 | 2-methylthiophene | cyclohexyl | | -N(C(=O)NHC(=O)CH₂-) (hydantoinyl) | 1 |

TABLE 10-continued

| Compound No. | A | B | R² | R³ | n |
|---|---|---|---|---|---|
| 210 | CH₃-C(=CH-S-)- | cyclohexyl | -N(CH(CH₃)CH₃... | 2,4-dioxoimidazolidinyl (with isopropyl) | 1 |
| 211 | CH₃-C(=CH-S-)- | 1,1-dimethylcyclohexyl | | 2-oxopyrrolidin-1-yl | 1 |
| 212 | CH₃-C(=CH-S-)- | spiro(cyclopropane-cyclopentane) | | 2-oxopyrrolidin-1-yl | 1 |
| 213 | CH₃-C(CH₃)=C(S-)- | cyclopentyl | | 2-oxopyrrolidin-1-yl | 1 |
| 214 | CH₃-C(CH₃)=C(S-)- | 1,1-dimethylcyclohexyl | | 2-oxopyrrolidin-1-yl | 1 |
| 215 | CH₃-C(CH₃)=C(S-)- | spiro(cyclopropane-cyclopentane) | | 2-oxopyrrolidin-1-yl | 1 |
| 216 | thienyl (S-) | cyclopentyl | | 2-oxopyrrolidin-1-yl | 1 |
| 217 | thienyl (S-) | spiro(cyclopropane-cyclopentane) | | 2-oxopyrrolidin-1-yl | 1 |
| 218 | CH₃-C(=CH-O-)- | cyclopentyl | | 2-oxopyrrolidin-1-yl | 1 |

TABLE 10-continued

| Compound No. | A | B | R² | R³ | n |
|---|---|---|---|---|---|
| 219 | CH₃-C(=CH-O-)- | cyclohexyl | -N(C(=O)NH-CH₂-C(=O)-) (hydantoinyl) | | 1 |
| 220 | (CH₃)₂C=C(CH₃)-O- | cyclopentyl | -N(pyrrolidin-2-on-1-yl) | | 1 |
| 221 | (CH₃)₂C=C(CH₃)-O- | 1,1-bis(methylene)cyclopropyl | -N(pyrrolidin-2-on-1-yl) | | 1 |
| 222 | phenyl | cyclohexyl | -N(hydantoinyl) | | 1 |
| 223 | phenyl | cyclohexyl | -N(5-ethyl-hydantoinyl), C₂H₅ | | 1 |
| 224 | F-phenyl | cyclohexyl | -N(hydantoinyl) | | 1 |
| 225 | Cl-phenyl | cyclohexyl | -N(hydantoinyl) | | 1 |
| 226 | phenyl | norbornyl | -N(hydantoinyl) | | 1 |

TABLE 10-continued
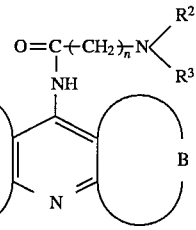
| Compound No. | A | B | R² | R³ | n |
|---|---|---|---|---|---|
| 227 |  |  | 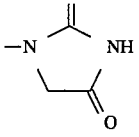 | | 1 |
| 228 |  |  |  | | 1 |
| 229 | 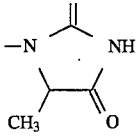 |  |  | | 1 |
| 230 |  | 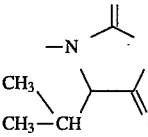 | 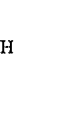 | | 1 |
| 231 |  |  | 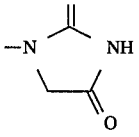 | | 1 |
| 232 |  |  |  | | 1 |
| 233 | 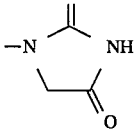 |  |  | | 1 |
| 234 |  | 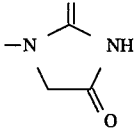 |  | | 1 |

TABLE 10-continued

| Compound No. | A | B | R² | R³ | n |
|---|---|---|---|---|---|
| 235 | CH₃-S- (methylthiovinyl) | cyclohexyl | -N(C=O)CH₂C(=O)NH (succinimide-like) | | 1 |

Test Example 1:

Na⁺ dependent high-affinity choline uptake ability (HACU) of the brain of a rat treated with AF64A AF64A was prepared from AF64 in accordance with the method of Fischer et al. (J. Pharmacol. Exp. Ther., 222, 140(1982)). AF64A (1.5 nmol/1.5 μl/side) was injected into both the lateral ventricles of a rat. One week after, the rat was decapitated and only the hippocampus was taken out. The hippocampus was homogenized with 0.32M of sucrose and centrifuged at 1000 g for 10 minutes. The supernatant thereof was further centrifuged at 20000 g for 20 minutes to obtain a crude synapse fraction. The crude synapse fraction was added with a compound of the present invention and incubated at 37° C. for 30 minutes. After adding [³H]choline (1 μM), the mixture was further incubated at 37° C. for 10 minutes. Another crude synapse fraction was incubated at 37° C. for 10 minutes and used as the control. The reaction was discontinued by filtering the mixture with suction on a Whatman GF/B filter. The radioactivity on the filter was measured by a liquid scintillation counter and the measured value was regarded as the amount of HACU. The amount of protein was determined in accordance with the method of Bradford (Anal. Biochem., 72, 248(1976)). The results are shown in Table 11.

TABLE 11

| | Improvement (% base on control) | | | | |
|---|---|---|---|---|---|
| Example No. | $10^{-8}$M | $10^{-7}$M | $10^{-6}$M | $10^{-5}$M | $10^{-4}$M |
| 1 | 7 | 11 | 8 | 2 | 2 |
| 2 | 6 | 10 | 7 | 8 | 11 |
| 3 | −1 | 13 | 7 | 23** | 7 |
| 5 | 20** | 4 | 18 | 19 | — |
| 6 | 3 | 10 | 4 | 10 | — |
| 9 | 0 | 7 | 5 | 13 | — |
| 10 | 11 | 15 | 26* | 44** | — |
| 11 | 11* | 10 | 10* | 10 | −1 |
| 12 | 14 | 8 | 17 | 31* | — |
| 15 | 3 | 5 | 7 | 11 | −4 |
| 16 | 9 | 2 | 9 | 4 | — |
| 17 | 7 | −1 | −2 | 3 | 20 |
| 19 | 4 | 10 | 14 | 6 | 13 |
| 21 | 11* | 9 | 11 | 19* | 4 |
| 22 | 0 | 1 | −3 | 10 | 6 |
| 25 | 21* | 19 | 19* | 31 | 22** |
| 26 | 4 | −3 | 9 | 14 | 2 |
| 27 | 5 | 18 | 5 | 18 | −11 |
| 30 | 8 | 17 | 13 | 28* | — |
| 34 | 10* | 13* | −3 | 14 | — |
| 35 | 11** | 17* | 20** | 21** | −16 |
| 36 | 18 | 15 | 3 | 19* | — |
| 39 | 9 | −7 | 13 | 16 | 2 |
| 41 | 8 | 8 | 19* | 25** | −4 |
| 42 | 1 | 18 | 17 | 9 | −13 |
| 45 | 0 | 2 | 6 | 14 | — |
| 52 | 6 | 13 | 11 | 10 | 7 |
| 54 | 5 | 18** | 15* | 14* | — |
| 55 | 20** | 25* | 26* | 36* | −30 |
| 58 | 4 | 5 | 7 | 25 | 15 |
| 59 | 5 | 16* | 22* | 30* | — |
| 61 | 14 | 3 | 21* | 25 | 23 |
| 63 | 10 | 13* | 19 | 31* | — |

[*P < 0.05]
[**P < 0.01]

What is claimed is:

1. A 4-acylaminopyridine derivative represented by the following formula (I):

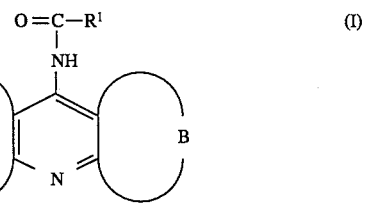

wherein R¹ represents a group represented by the following formula (II):

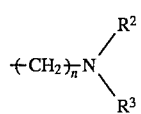 (II)

wherein $R^2$ and $R^3$ together with the nitrogen atom to which both $R^2$ and $R^3$ are attached represent

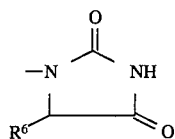

wherein $R^6$ represents a hydrogen atom or $C_1$–$C_6$ alkyl group, and n represents 0 or an integer from 1 to 3;

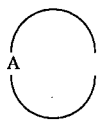 represents 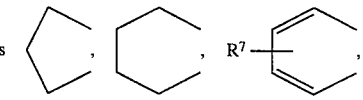,

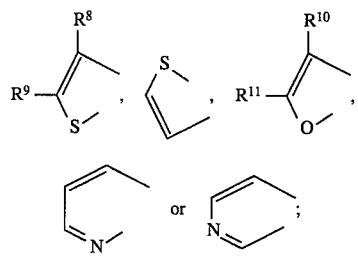

wherein $R^7$ represents a hydrogen atom, $C_1$–$C_6$ alkyl group or halogen atom, $R^8$ and $R^9$ independently represents a hydrogen atom or $C_1$–$C_4$ alkyl group, $R^{10}$ and $R^{11}$ independently represents a hydrogen atom or $C_1$–$C_4$ alkyl group; and

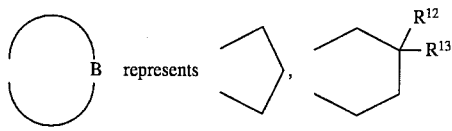

wherein each of $R^{12}$ and $R^{13}$ independently represents a hydrogen atom or $C_1$–$C_4$ alkyl group or $R^{12}$ and $R^{13}$ may be combined together to form a $C_2$–$C_6$ alkylene group,

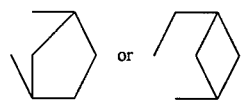

and a pharmaceutically acceptable acid addition salt thereof.

2. A pharmaceutical composition comprising pharmaceutically effective amount of the 4-acylaminopyridine derivative according to claim 1 or the pharmaceutically acceptable acid addition salt according to claim 1, and a pharmaceutically acceptable adjuvant.

\* \* \* \* \*